United States Patent [19]

Weiner et al.

[11] 4,202,892
[45] May 13, 1980

[54] BIOCIDAL METHYLADAMANTYL HYDRAZINES AND PHARMACEUTICAL COMPOSITIONS CONTAINING THEM

[75] Inventors: Ben-Zion Weiner; Jeffrey Sterling; Raul Suchi, all of Jerusalem; Haim Yellin, Ramat Gan, all of Israel

[73] Assignee: Teva Pharmaceutical Industries, Ltd., Jerusalem, Israel

[21] Appl. No.: 963,114

[22] Filed: Nov. 22, 1978

[30] Foreign Application Priority Data

Nov. 22, 1977 [IL] Israel .......................................... 53441

[51] Int. Cl.² ..................... A61K 31/33; A61K 27/00; A61K 31/15; C07C 109/02
[52] U.S. Cl. ................................ 424/244; 260/239 B; 260/326.5 FM; 260/326.86; 260/563 P; 260/569; 424/248.56; 424/250; 424/258; 424/263; 424/267; 424/273 R; 424/274; 424/276
[58] Field of Search ................... 424/327, 244, 248.56, 424/263, 267, 250, 274, 305, 319, 258, 273, 276; 260/239 B, 268 R, 288 R, 293.65, 296 R, 328.86, 563 P, 569; 544/59, 274.5 R; 548/308; 560/116; 562/439, 499

[56] References Cited

U.S. PATENT DOCUMENTS

| | | | |
|---|---|---|---|
| 3,719,710 | 3/1973 | Thomas et al. | 260/563 P |
| 4,061,774 | 12/1977 | Chakrabarti et al. | 424/325 |

*Primary Examiner*—Leonard Schenkman

*Attorney, Agent, or Firm*—Browdy and Neimark

[57] ABSTRACT

The invention provides novel 1- or 2-adamantylmethyl hydrazines of the general formula A

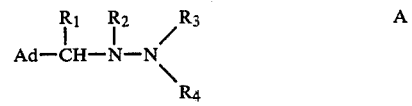

In this formula Ad is 1- or 2-adamantyl, $R_1$ and $R_2$ are the same or different and are each hydrogen or a lower unsubstituted or substituted alkyl group of 1–4 carbon atoms; $R_3$ and $R_4$ are the same or different and are each hydrogen, an unsubstituted or substituted radical being a lower alkyl group of 1–4 carbon atoms a lower alkanoic acid radical of 2–4 carbon atoms or a lower alkyl ester thereof, adamantyl, aryl, aralkyl in which the alkyl moiety has 1–4 carbon atoms or an unsubstituted or substituted heterocyclic radical of aromatic character; or $R_3$ and $R_4$ together with the nitrogen atom to which they are attached form a cyclic radical or non-aromatic character.

The invention further provides pharmaceutically acceptable acid addition salts of the above compounds.

Several methods of preparation of the new compounds are described.

The novel compounds according to the invention possess valuable antifungal (human and plant), antiviral, antiprotozoal and antimicrobial properties.

44 Claims, No Drawings

BIOCIDAL METHYLADAMANTYL HYDRAZINES AND PHARMACEUTICAL COMPOSITIONS CONTAINING THEM

The present invention relates to novel adamant-1- or -2-ylmethyl hydrazines, to pharmaceutically acceptable acid addition salts thereof and to methods of preparing the novel compounds and their salts.

Specifically the invention provides 1- or 2-adamantylmethyl hydrazines of the general formula A

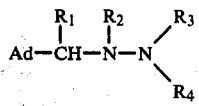

wherein Ad is 1- or 2-adamantyl, $R_1$ and $R_2$ are the same or different and are each hydrogen or a lower unsubstituted or substituted alkyl group of 1–4 carbon atoms; $R_3$ and $R_4$ are the same or different and are each hydrogen, an unsubstituted or substituted radical being a lower alkyl group of 1–4 carbon atoms a lower alkanoic acid radical of 2–4 carbon atoms or a lower alkyl ester thereof, adamantyl, aryl, aralkyl in which the alkyl moiety has 1–4 carbon atoms or an unsubstituted or substituted heterocyclic radical of aromatic character; or $R_3$ and $R_4$ together with the nitrogen atom to which they are attached form a cyclic radical of non-aromatic character; and pharmaceutically acceptable acid addition salts thereof.

The term "lower alkanoic acid or ester radical" refers herein to a radical which is linked to the hydrazine nitrogen atom at one of the noncarboxylic carbon atoms thereof, i.e. at a carbon atom forming part of the lower alkyl moiety of said radical.

Where $R_3$ and/or $R_4$ is a lower alkyl ester of a lower alkanoic acid of 2–4 carbon atoms, the ester forming lower alkyl radical may, for example, be methyl, ethyl, propyl or butyl.

Examples of heterocyclic radicals of aromatic character for which either of $R_3$ and $R_4$ may stand are pyridinyl or quinolinyl.

Examples of cyclic radicals formed by $R_3$, $R_4$ and the nitrogen atom to which they are attached are piperidino, homopiperidino, pyrrolidino, morpholino, thiomorpholino, hydantoino, piperazine or heptamethyleneimino radicals all of which radicals may be substituted.

A compound of formula A in which $R_2$ is hydrogen can be prepared in accordance with the invention by reacting a compound of either of formulae B and C:

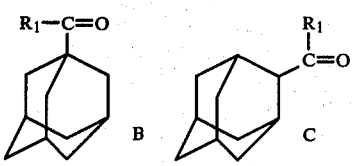

in which $R_1$ is as in formula A, with a hydrazine compound in which at least one of the nitrogens does not bear any substituent to produce the corresponding hydrazone, and reducing the latter.

In the above process the reduction may be effected in any suitable conventional way, e.g. with a reducing agent such as sodium cyanoborohydride or by catalytic hydrogenation using any suitable conventional hydrogenation catalyst such as, for example, Adam's Catalyst.

The above embodiment for the preparation of compounds according to the invention is illustrated in the following Reaction Scheme I in which $R_1$, $R_3$ and $R_4$ have the same meanings as in formula A and the $R_1C=O$ group is depicted in the 1-position:

Reaction Scheme I

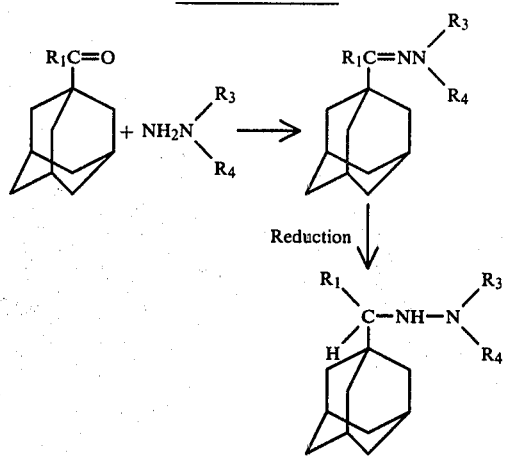

This general method was applied in accordance with the invention in the preparation of the following adamantylmethylhydrazine derivatives:

1-(Adamant-1'-ylmethyl)-2-methylhydrazine
1-(Adamant-1'-ylmethyl)-2,2-dimethylhydrazine
1-(Adamant-1'-ylmethyl)-2-[1''-(2''-hydroxyethyl)]hydrazine
1-(Adamant-1'-ylmethyl)-2-benzylhydrazine
1-(Adamant-1'-ylmethyl)-2-phenethylhydrazine
1-(Adamant-1'-ylmethyl)-2-(p-bromophenyl)hydrazine
1-(Adamant-1'-ylmethyl)-2,2-diphenylhydrazine
1-(Adamant-1'-ylmethyl)-2-(m-trifluoromethylphenyl)hydrazine
1-(Adamant-1'-ylmethyl)-2-(o-carboxyphenyl)hydrazine
1-(Adamant-1'-ylmethyl)-2-[4''-(7''-chloroquinolinyl)]hydrazine
1-(Adamant-1'-ylmethylamino)pyrrolidine
1-(Adamant-1'-ylmethylamino)-2-methylpyrrolidine
1-(Adamant-1'-ylmethylamino)piperidine
1-(Adamant-1'-ylmethylamino)homopiperidine
1-(Adamant-1'-ylmethylamino)heptamethyleneimine
4-(Adamant-1'-ylmethylamino)morpholine
1-(Adamant-1'-ylmethylamino)-4-methylpiperazine
1-(Adamant-1'-ylmethylamino)-4-(m-trifluoromethylphenyl)piperazine
1-(Adamant-2'-ylmethyl)-2,2-dimethylhydrazine
1-(Adamant-2'-ylmethyl)-2-(pyrid-2''-yl)hydrazine
1-(Adamant-2'-ylmethylamino)pyrrolidine
1-(Adamant-2'-ylmethyl)-2-(1'-adamantyl)hydrazine
1-[(Adamant-1'-yl)ethyl]hydrazine
1-[1'-(Adamant-1''-yl)ethyl]-2-methylhydrazine
1-[1'-(Adamant-1''-yl)ethyl]-2-(m-trifluoromethylphenyl)hydrazine
1-(Adamant-2'-ylmethylamino)piperidine
1-(Adamant-1'-ylmethylamino)thiomorpholine
1-(Adamant-1'-ylmethylamino)hydantoin
1-(Adamant-1'-ylmethyl)-2-butylhydrazine By another embodiment adamantylmethyl hydrazines of formula A are prepared by condensation of 1- or 2-haloalkyl adamantane with a hydrazine at elevated temperature and pressure, e.g. in a sealed tube at 150°, in accordance with the following Reaction Scheme II in which $R_1$, $R_2$, $R_3$ and $R_4$ are as in formula A and the haloalkyl group is depicted in the 1-position, Hal being halogen:

2'-ylmethyl)-1-methylhydrazine was, for example, prepared.

[2-(Adamant-1'-ylmethyl)hydrazino]alkanoic acid esters, their acid addition salts and the corresponding free acids can be prepared in accordance with the invention by a modification of the foregoing embodiment employing a hydrazino acid alkyl ester. This modification is shown in the following Reaction Scheme IV in which $R_1$ is as in formula A, $R_5$ is hydrogen methyl or ethyl and $R_6$ is a lower alkyl and the group $R_1C=O$ is depicted in the 1-position:

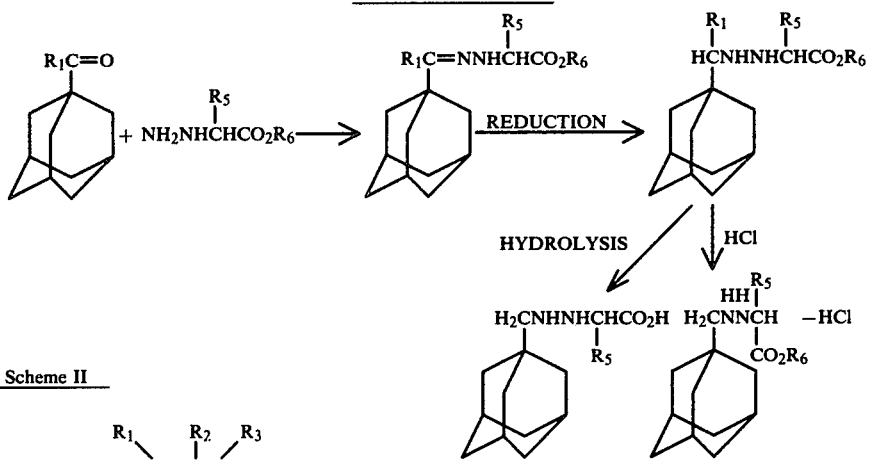

Reaction Scheme IV

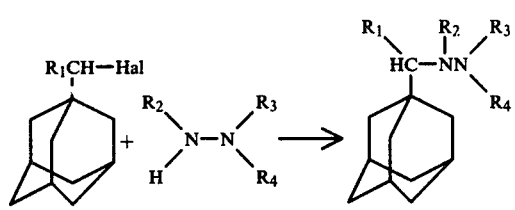

Reaction Scheme II

In this manner (adamant-1-ylmethyl)hydrazine and 1-(adamant-1'-ylmethyl)-1-methylhydrazine were, for example, prepared.

By yet another embodiment 1- or 2-adamantane carboxylic acid chloride is reacted with a hydrazine having at least one free hydrogen and the resulting hydrazide is reduced. This embodiment is shown in the following Reaction Scheme III in which $R_2$, $R_3$ and $R_4$ are as in formula A and the carboxy chloride group is depicted in the 2-position:

For the reduction a hydrogen generating compound such as, e.g., sodium cyanoborohydride may, for example, be used. The hydrolysis is best effected under mild conditions, e.g. by ion exchange or by refluxing with conc. HCl. A suitable ionexchanger is, for example, the one known by the commercial designation "Amberlite I R 120 (H)".

As representative examples in this way were synthesized:
Ethyl [2-(adamant-1'-ylmethyl)hydrazino]acetate
[2-(adamant-1-ylmethyl)hydrazine]acetic acid, and
α-[2-(adamant-1'-ylmethyl)hydrazino]butanoic acid.

Attempts at using in the above embodiment free hydrazino acids were unsuccessful, presumably due to their existence as zwitterions which destroys the nucleophilic character of the hydrazine.

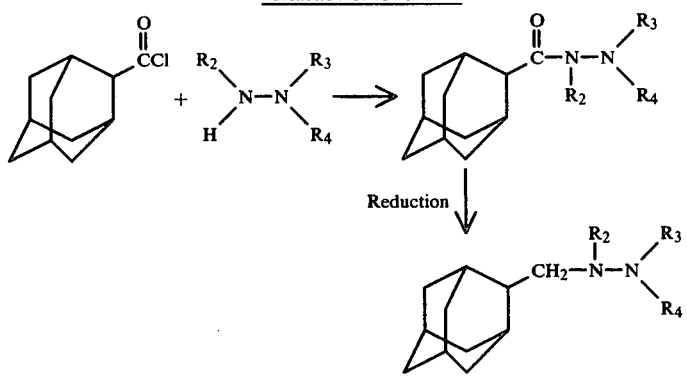

Reaction Scheme III

For the reduction a hydrogen generating compound such as, for example, lithium aluminium hydride may be used. In this way, using methylhydrazine, 1-(adamant- By yet another embodiment for the preparation of a compound of formula A in which $R_1$ and $R_2$ are hydrogen, a compound of either of formulae B and C is reacted with an acyl protected hydrazine in which the non-protected nitrogen does not bear any substituent, the resulting protected hydrazone is reduced and the protected adamantylhydrazine so obtained is hydrolyzed. This embodiment is shown in the following Reaction Scheme V in which the $R_1C=O$ group is depicted in the 1-position:

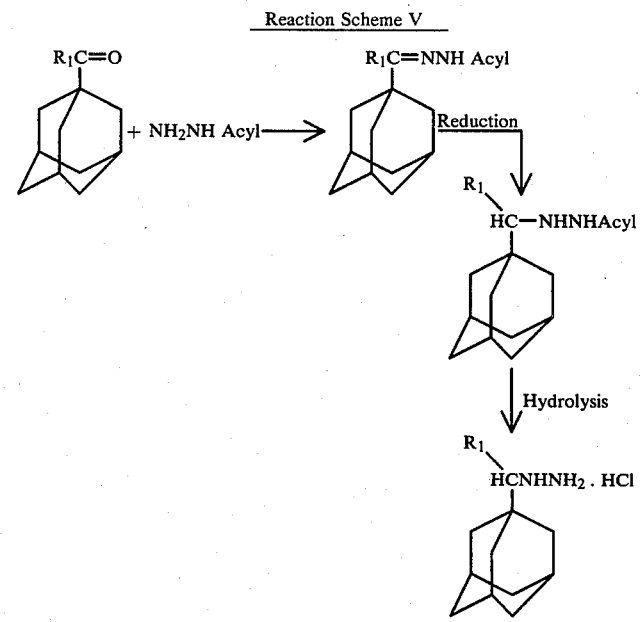

For the reduction it is again possible to use, for example, a hydrogen generating compound such as, e.g., sodium cyanoborohydride. For the hydrolysis of the acyl group a strong mineral acid such as, for example, hydrochloric acid can be used. In this way (adamant-1-ylmethyl)hydrazine was for example, prepared.

By a modification of the above embodiment the acylated hydrazine is N-alkylated prior to hydrolysis. For the alkylation it is possible to use, for example, a methyl- or ethylfluorosulfonate. The N-alkylated hydrazine is then hydrolyzed as above. The modification is shown in the following Reaction Scheme VI in which $R_2$ is as defined in formula A and the hydrazino moiety is depicted in the 1-position and the alkylating agent is methylfluorosulfonate:

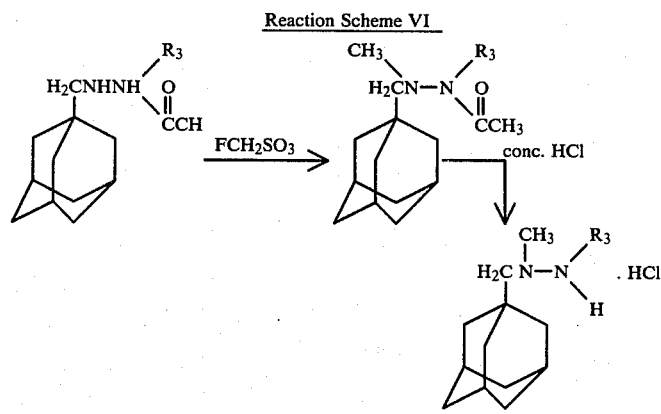

In this way 1-(adamant-1'-ylmethyl)-1,2-dimethylhydrazine was, for example, prepared.

By yet another embodiment for the preparation of a compound of either formulae B and C in which $R_3$ and $R_4$ are both hydrogen but $R_2$ is not hydrogen, a nitrogen-nitrogen bond is formed between a suitable disubstituted amine and an aminating agent, e.g. sodium nitrite followed by reduction with a reducing agent, such as lithium aluminium hydride.

For example, (adamant-1'-ylmethyl)isopropylamine was reacted under acidic conditions with sodium nitrite and the resulting N-nitroso compound reduced with lithium aluminium hydride to yield 1-(adamant-1'-ylmethyl)-1-isopropylhydrazine. (Scheme VII, R=isopropyl for example).

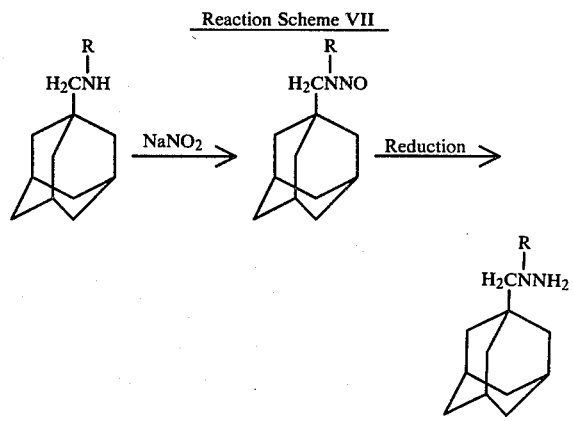

Where in any compound according to the present invention obtained in accordance with any of the foregoing methods a free hydrogen atom of the hydrazine moiety is to be substituted, such substitution may be effected in accordance with known methods, e.g. alkylation with suitable alkylating agents such as treatment with a powerful base followed by an alkyl halide. For example, 1-(adamant-1'-ylmethylamino)pyrrolidine obtained, e.g. in accordance with Scheme I, yields upon treatment with butyllithium in dry tetrahydrofuran followed by one equivalent of methyl iodide the corresponding 1-[(adamant-1'-ylmethyl)methylamino]pyrrolidine.

Furthermore, alkylation of any compound according to the present invention containing one unsubstituted nitrogen in the hydrazine moiety may also be accomplished by condensing said (adamantylmethyl)hydrazine with a suitable aldehyde or ketone. The resulting hydrazone may be reduced by any of the classical reduction methods employed in reaction Scheme I. For example (adamanty-1'-ylmethyl)-hydrazine obtained, e.g. in accordance with Reaction Scheme II, yields upon treatment with acetone, and subsequent reduction with sodium cyanoborohydride, the corresponding 1-(adamant-1'-ylmethyl)-2-isopropylhydrazine (see Scheme VIII, $R_1=R_2=CH_3$ for example only).

Reaction Scheme VIII

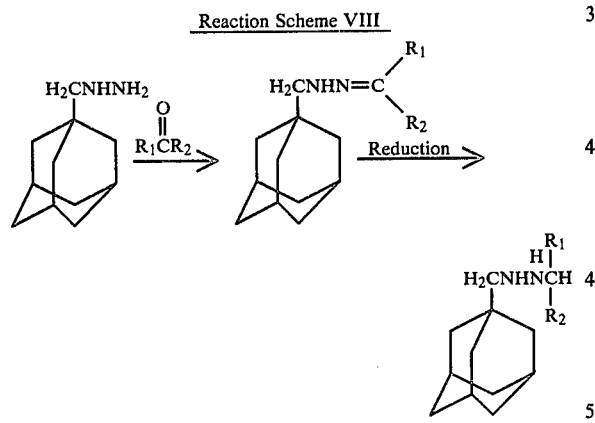

A further modification of the aforementioned alkylation uses a cyclic carboxylic acid anhydride for example, as an alkylating agent. The resulting cyclic hydrazide is then reduced in a strong reducing agent such as lithium aluminium hydride. For example, (adamant-1-ylmethyl)hydrazine was treated with methylsuccinic anhydride in refluxing toluene with provision for water removal. The resulting hydrazide was reduced with lithium aluminium hydride to yield 1-(adamant-1'-ylmethylamino)-3-methylpyrrolidine (Scheme IX, $R_1=CH_3$ for example).

Reaction Scheme IX

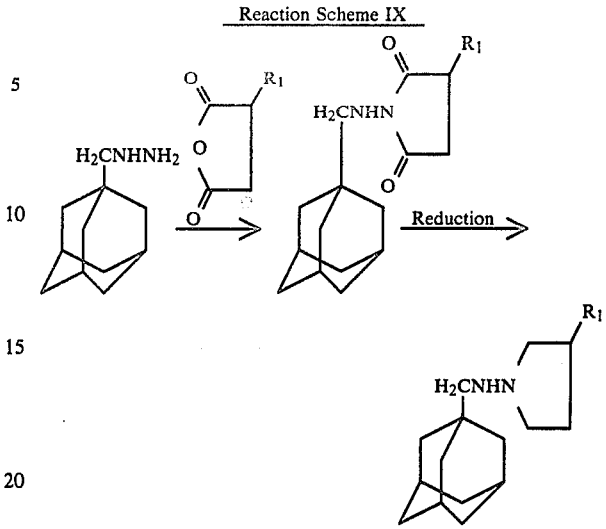

Quite generally, compounds according to the invention in which the hydrazine moiety is mono-substituted may be converted into di-substituted compounds where the substitution is either on the same nitrogen atom or on different nitrogen atoms and any compound according to the invention in which the hydrazine moiety is di-substituted may be converted by further substitution into the corresponding compound in which the hydrazine moiety is tri-substituted.

In the methods of preparation described hereinbefore the compounds according to the invention are obtained either in the free base form or as acid addition salts. Where a free base is obtained it can be converted into an acid addition salt by reaction with a pharmaceutically acceptable acid as known per se and conversely, where the product first obtained is an acid addition salt and the free base is desired the salt is converted into the free base by reaction with a base, again as known per se.

Furthermore, it is possible to convert an acid addition salt of a compound of formula A into a different one.

Novel compounds according to the invention of the general formula A possess valuable antifungal (human and plant), antiviral, antiprotosoal and antimicrobial properties. Compounds according to the invention are also active against infections caused by such viruses as vaccinia, herpes simplex or influenza or by protozoan parasites such as leishmania and trypanosoma, or by microorganisms such as leptospira, and also possess central nervous system (CNS) activity.

For administration to patients the novel compounds according to the invention are compounded with pharmaceutically acceptable carriers and, if desired, with other pharmaceutically active substances and/or pharmaceutically conventional adjuvants.

The invention also provides compositions containing each as active ingredient a compound of formula A together with an acceptable carrier. Where such compositions are pharmaceutical the carrier must be pharmaceutically acceptable. In case of veterinary compositions or compositions for agricultural use the carriers are selected accordingly.

The invention is illustrated by the following examples to which it is not limited, all temperature indications being in centigrade.

EXAMPLE 1

1-(Adamant-1'-ylmethyl)-2-methylhydrazine hydrochloride

A methanolic solution of 1.2 g (7 mmol) of 1-adamantylaldehyde and 1 g (21 mmol) of methylhydrazine was refluxed for 2 hours at which time the volatiles were removed in vacuo. The resulting oil was taken up in ether, washed with water, dried and concentrated to 1.4 g hydrazone which was reduced with an excess of sodium cyanoborohydride in slightly acidified ethanol. After 1 hour the reaction was basified with 10% aq. sodium hydroxide. Solvent evaporation followed by ether extraction, water wash and treatment with hydrogen chloride gave 900 mg (56%) of the title compound.

mp 236°–238° (d), (ethylacetate/isopropanol)
nmr (CDCl$_3$/TFA) δ2.9 (S, 3H), 2.8 (S, 2H).
Anal. calcd for C$_{12}$H$_{23}$N$_2$Cl: C, 62.49; H, 10.06; N, 12.16; Cl, 15.38; Found: C, 62.62; H, 10.03; N, 12.55; Cl, 15.65.

Compounds described in the following Examples 2 to 13 and 24 to 36 were prepared by the same method as Example 1, except that 1 equivalent of the appropriate hydrazine derivative was used.

EXAMPLE 2

1-(Adamant-1'-ylmethyl)-2,2-dimethylhydrazine hydrochloride hemi-hydrate

The title compound was obtained in 35% yield by using 1,1-dimethylhydrazine instead of methylhydrazine as in Example 1.

mp 284°–5° (d), (isopropanol)
nmr (CDCl$_3$/TFA) δ3.0 (s., 6H), 2.7 (S, 2H).
Anal calcd for C$_{13}$H$_{26}$N$_2$O$_{\frac{1}{2}}$Cl: C, 61.54; H, 10.25; H, 11.09; Cl, 14.00; Found: C, 61.21; H, 10.65; H, 11.49; Cl, 13.76.

EXAMPLE 3

1-(Adamant-1'-ylmethyl)-2-benzylhydrazine hydrochloride

The title compound was obtained in 54% yield by using benzylhydrazine instead of methylhydrazine as in Example 1.

mp 232°–5° (d), (isopropanol/water)
nmr (CDCl$_3$/TFA) δ7.3 (S, 5H), 4.3 (S, 2H), 2.8 (S, 2H).
Anal calcd for C$_{18}$H$_{27}$N$_2$Cl: C, 70.43; H, 8.87; N, 9.13; Cl, 11.57; Found: C, 70.26; H, 8.98, N, 9.06; Cl, 11.68

EXAMPLE 4

1-(Adamant-1'-ylmethyl)-2,2-diphenylhydrazine hydrochloride

The title compound was obtained in 48% yield by using 1,1-diphenylhydrazine instead of methylhydrazine as in Example 1.

mp 162°–164° (d), (ethylacetate)
nmr (CDCl$_3$) δ6.9–7.6 (m, 10H), 3.0 (S, 2H)
mass spectrum (m/e)M+ =332.

EXAMPLE 5

1-(Adamant-1'-ylmethyl)-2-(m-trifluoromethylphenyl)-hydrazine hydrochloride hemi-hydrate The title compound was obtained in 52% yield by using (m-trifluoromethylphenyl)hydrazine instead of methylhydrazine as in Example 1.

mp 200°–203° (d), (ethylacetate)
nmr (CDCl$_3$/TFA) δ7.1–7.4 (m, 4H); 3.0 (S, 2H).
Anal calcd for C$_{18}$H$_{25}$N$_2$F$_3$ClO$_{1/2}$: C, 58.42; H, 6.81; N, 7.88; Cl, 9.60; Found: C, 58.38; H, 6.78; N, 7.88; Cl, 9.72.

EXAMPLE 6

1-(Adamant-1'-ylmethyl)-2-(o-carboxyphenyl)hydrazine

The title compound was obtained in 50% yield by using N-aminoanthranilic acid instead of methylhydrazine as in Example 1.

mp 212°–3° (d), (ethyl acetate/petroleum ether).
nmr (CDCl$_3$/TFA) δ3.1 (S, 2H).
Anal calcd for C$_{18}$H$_{24}$N$_2$O$_2$: C, 71.95; H, 8.06; N, 9.32; Found: C, 72.00; H, 8.31; N, 9.14.

EXAMPLE 7

1-(Adamant-1'-ylmethylamino)pyrrolidine hydrochloride

The title compound was obtained in 64% yield by using 1-aminopyrrolidine instead of methylhydrazine as in Example 1.

mp 260°–264° (d), (isopropanol)
nmr (CDCl$_3$/TFA) δ2.7 (S, 2H).
Anal calcd for C$_{15}$H$_{27}$N$_2$Cl: C, 66.49; H, 10.04; N, 10.34; Cl, 13.11; Found: C, 66.62; H, 9.93; N, 10.32; Cl, 13.19.

EXAMPLE 8

1-(Adamant-1'-ylmethylamino)piperidine hydrochloride

The title compound was obtained in 47% yield by using 1-aminopiperidine instead of methylhydrazine as in Example 1.

mp 289°–291° (d), (isopropanol)
nmr (CDCl$_3$/TFA) δ2.7 (S, 2H)
Anal calcd for C$_{16}$H$_{29}$N$_2$Cl: C, 67.43; H, 10.18; N, 9.83; Cl, 12.47; Found: C, 67.69; H, 10.50; N, 9.64; Cl, 12.36.

EXAMPLE 9

4-(Adamant-1'-ylmethylamino)morpholine hydrochloride hemi-hydrate

The title compound was obtained in 45% yield by using 4-aminomorpholine instead of methylhydrazine as in Example 1.

mp 274°–276° (d), (isopropanol)
nmr (CDCl$_3$/TFA) δ2.8 (S, 2H).
Anal calcd for C$_{15}$H$_{28}$N$_2$ClO$_{1.5}$: C, 60.87; H, 9.54; N, 9.46; Cl, 12.00; Found: C, 61.10; H, 9.37; N, 9.80; Cl, 11.90.

EXAMPLE 10

1-(Adamant-1'-ylmethylamino)-4-methylpiperazine dihydrochloride hydrate

The title compound was obtained in 35% yield by using 1-amino-4-methylpiperazine instead of methylhydrazine as in Example 1.

mp 286°–287° (d), (ethanol)
nmr (CDCl$_3$/TFA) δ2.6–4/0 (m, 13H)
Anal calcd for C$_{16}$H$_{33}$N$_3$Cl$_2$O: C, 54.19; H, 9.40; N, 11.85; Cl, 20.04; Found: C, 54.52; H, 9.12; N, 11.18; Cl, 20.56.

EXAMPLE 11

1-(Adamant-1'-ylmethylamino)-4-(m-trifluoromethyl-phenyl)piperazine hydrochloride hemi-hydrate The title compound was obtained in 57% yield by using 1-amino-4-(m-trifluoromethylphenyl)piperazine instead of methylhydrazine as in Example 1.

mp 261°–265° (d), (methanol)
nmr (CDCl$_3$/TFA) δ3.9 (S, 8H), 3.0 (S, 2H)
Anal calcd for C$_{22}$H$_{32}$N$_3$ClF$_3$O$_{\frac{1}{2}}$: C, 60.21; H, 7.30; N, 9.58; Cl, 8.10; F, 13.00; Found: C, 60.44; H, 7.30; N, 9.62; Cl, 8.22; F, 12.52.

EXAMPLE 12

1-(Adamant-2'-ylmethyl)-2,2-dimethylhydrazine hydrochloride

The title compound was obtained in 30% yield by using 2-adamantylaldehyde and 1,1-dimethylhydrazine instead of 1-adamantylaldehyde and methylhydrazine respectively as in Example 1.

mp 217°–220° (d), (ethyl acetate/methylene chloride)
nmr (CDCl$_3$) δ3.15 (d, 2H); 2.86 (S, 6H)
Anal calcd for C$_{13}$H$_{25}$N$_2$Cl: N, 11.45; Cl, 14.52; Found: N, 11.43; Cl, 14.46.

EXAMPLE 13

1-(Adamant-2'-ylmethyl)-2-(pyrid-2''-yl)hydrazine hydrochloride

The title compound was obtained in 55% yield by using 2-adamantylaldehyde and (pyrid-2'-yl)hydrazine instead of 1-adamantylaldehyde and methylhydrazine respectively as in Example 1.

mp 135°–140° (d), (ethyl acetate)
nmr (CDCl$_3$/TFA) δ3.33–3.60 (d, 2H).
mass spectrum (m/e) M$^+$=257.

EXAMPLE 14

(Adamant-1-ylmethyl)hydrazine hydrochloride 4.0 g (120 mmol) of anhydrous hydrazine and 2.3 g (12 mmol) of 1-chloromethyladamantane were introduced into a sealable tube under nitrogen atmosphere. The tube was sealed and heated at 150° for 16 hours. After cooling to room temperature the contents were suspended in methanol, treated with a solution 0.5 g of sodium hydroxide in 1.5 ml of water, and the volatiles removed in vacuo. The resulting solid was extracted with ether and the solution dried with magnesium sulfate and treated with hydrogen chloride to give 1 g of the title compound (38% yield).

mp 256°–258° (d), (isopropanol)
nmr (CDCl$_3$/TFA) δ3.3 (S, 2H)
Anal calcd for C$_{11}$H$_{21}$N$_2$Cl: C, 60.97; H, 9.78; N, 12.94; Cl, 16.37; Found: C, 61.20; H, 9.71; N, 12.85; Cl, 16.77.

EXAMPLE 15

1-Methyl-1-(adamant-1'-ylmethyl)hydrazine hydrochloride hydrate

The procedure of Example 14 was followed using methylhydrazine instead of anhydrous hydrazine. The resulting ether solution containing the 2 possible condensation products, the title compound and the 2-methyl isomer, was stored at about 5° for 4 days. Thereafter treatment with hydrogen chloride caused the title compound to crystallize from the solution in 95% purity (35% yield).

mp 196°–197° (d), (ethyl acetate/methylene chloride)
nmr (CDCl$_3$/TFA) δ3.05 (S, 3H), 2.95 (S, 2H)
Anal calcd for C$_{12}$H$_{25}$N$_2$ClO: C, 57.90; H, 10.13; N, 11.25; Cl, 14.27; Found: C, 57.86; H, 10.24; N, 11.09; Cl, 14.12.

EXAMPLE 16

1-Methyl-1-(adamant-2'-ylmethyl)hydrazine hydrochloride

To 7 g of methylhydrazine in 25 ml of ethylacetate was added 5.4 g of 2-adamantylcarboxylic acid chloride in 25 ml of the same solvent. After 15 minutes additional stirring the reaction was washed with a solution of ammonium chloride and concentrated to 4.5 g of hydrazide. The hydrazide was reduced with 1.1 g of lithium aluminum hydride in refluxing tetrahydrofuran for $\frac{1}{2}$ hour.

After cooling the reaction was poured into aqueous ammonium chloride and extracted 2 times with methylenechloride. The combined organic layers were dried over magnesium sulfate and solvent removed in vacuo. The resulting oil was dissolved in ether and treated with hydrogen chloride to give 2.4 g of the title compound (40% yield).

mp 224°–6° (d), (ethyl acetate)
nmr (CDCl$_3$) δ3.28 (d, 2H), 2.96 (S, 3H)
Anal calcd for C$_{12}$H$_{23}$ClN$_2$: C, 62.47; H, 9.97; N, 12.14; Cl, 15.40; Found: C, 62.67; H, 9.95; N, 12.10; Cl, 15.10.

EXAMPLE 17

Ethyl [(2-adamant-1'-ylmethyl)hydrazino]acetate hydrochloride

The procedure of Example 1 was followed using ethyl hydrazino-acetate instead of methylhydrazine, to give the title compound in 24% yield.

mp 188°–190° (d), (ethyl acetate)
nmr (CDCl$_3$) δ4.2 (q, 2H); 4.0 (S, 1H); 2.9 (S, 1H); 1.3 (t, 3H)
Anal calcd for C$_{15}$H$_{27}$N$_2$O$_2$Cl: C, 59.50; H, 8.92; Found: C, 59.36; H, 8.70.

EXAMPLE 18

[2-(Adamantyl-1'-ylmethyl)hydrazino]acetic acid hydrochloride

The hydrazino ester hydrochloride (3 g) of Example 17 was hydrolyzed with 2 g of Amberlite IR 120 (H) in refluxing water for 5 hrs to give the title compound in 25% yield after filtration and evaporation of solvent.

mp (178°–179° (isopropanol, ethyl acetate)
nmr (CDCl$_3$/TFA) δ4.0 (S, 2H), 3.0 (S, 2H).
Anal calcd for C$_{13}$H$_{23}$N$_2$O$_2$Cl: C, 56.79; H, 8.45; N, 10.19; Found: C, 57.00; H, 8.19; N, 9.78.

EXAMPLE 19

(Adamant-1-ylmethyl)hydrazine hydrochloride

The title compound was also prepared in analogy with Example 1 using acetylhydrazine instead of methylhydrazine. The acetyl group was cleaved by 2 hours reflux in conc. HCl, giving a product with identical properties to those of Example 14 (58% yield).

EXAMPLE 20

1,2-Dimethyl-1-(adamant-1'-ylmethyl)hydrazine hydrochloride

The procedure of Example 1 was followed using 1-acetyl-1-methylhydrazine instead of methylhydrazine. After reduction, the resulting acetylhydrazine was treated with one equivalent of methyl fluorosulfonate in methyl acetate at 0°. After stirring for 2 hours the reaction was poured into 10% aq sodium hydroxide and extracted with methylene chloride, the solvent removed and the residue was treated with conc. HCl and refluxed for 1 hour to give the title compound upon cooling.

mp 176°–179° (d), (ethyl acetate)

nmr (CDCl$_3$) $\delta$2.8 (S, 3H); 2.7 (S, 3H); 2.6 (S, 2H)

Anal calcd for C$_{13}$H$_{25}$N$_2$Cl: C, 63.75; H, 10.30; N, 11.44; Cl, 14.51; Found: C, 63.81; H, 10.40; N, 11.44; Cl, 14.94.

EXAMPLE 21

[1-(Adamant-1'-yl)ethyl]hydrazine hydrochloride

The procedure of Example 19 was followed using acetyladamantane instead of 1-adamantylaldehyde to give the title compound in 26% yield.

mp 212°–214° (d), (isopropanol)

nmr (CDCl$_3$/TFA) $\delta$2.95 (q, 1H, J=7 Hz), (d, 3H, J=7 Hz).

Anal calcd for C$_{12}$H$_{23}$N$_2$Cl: C, 62.49; H, 10.06; N, 12.16; Cl, 15.38; Found: C, 62.23; H, 10.03; N, 12.61; Cl, 15.09.

EXAMPLE 22

1-[1'-(Adamant-1''-yl)ethyl]-2-methylhydrazine hydrochloride

A solution of 1.8 g (10 mmol) of acetyladamantane and 600 mg (13 mmol) of methylhydrazine was refluxed in 150 ml of benzene with continuous removal of water via a Dean-Stark Apparatus.

After 2½ hours the reaction was cooled the volatiles removed in vacuo leaving 1.7 g oil which was reduced with 800 mg of sodium cyanoborohydride according to the procedure of Example 1. Treatment of the resulting ether solution with hydrogen chloride gave 900 mg of the title compound (37% yield).

mp 239°–241° (d), (acetone)

nmr (CDCl$_3$/TFA) $\delta$1.3 (d, 3H)

Anal calcd for C$_{13}$H$_{25}$N$_2$Cl: C, 63.75; H, 10.30; N, 11.44; Cl, 14.49; Found: C, 63.71; H, 10.60; N, 11.29; Cl, 14.90.

EXAMPLE 23

1-[1'-(Adamant-1''-yl)ethyl]-2-(m-trifluoromethylphenyl)hydrazine hydrochloride hemi-hydrate Following the procedure of Example 5, but using 1-acetyladamantane instead of 1-adamantylaldehyde the title compound was ontained in 37% yield.

mp 198°–200° (d), (ethyl acetate)

nmr (DMSO-d$_6$) $\delta$1.25 (d, 3H) Anal calcd for C$_{19}$H$_{27}$N$_2$ClF$_3$O$_{\frac{1}{2}}$: C, 59.42; H, 7.08; N, 7.29; Found: C, 59.27; H, 6.92; N, 7.06.

EXAMPLE 24

1-(Adamant-1'-ylmethyl)-2-[1''-(2''-hydroxyethyl)]hydrazine hydrochloride

The title compound was obtained in 42% yield by using 2-hydrazinoethanol instead of methylhydrazine as in Example 1 except that the resulting hydrazone was reduced with 50 psi H$_2$ on 10% palladium on carbon.

mp 194° (d), (methanol/ethylacetate)

nmr (CDCl$_3$/TFA) $\delta$3.4–4.4 (m, 2H), 3.3–3.6 (m, 2H); 3.0 (s, 2H)

Anal calcd for C$_{13}$H$_{25}$ClN$_2$O: C, 59.88; H, 9.60; N, 10.75; Cl, 13.63; Found: C, 59.71; H, 9.74; N, 10.94; Cl, 13.65.

EXAMPLE 25

1-(Adamant-1'-ylmethyl)-2-phenethylhydrazine dihydrate

The title compound was obtained in 29% yield by using phenethylhydrazine instead of methylhydrazine as in Example 1.

mp 231°–235° (d), (isopropanol/ether)

nmr (CDCl$_3$/TFA) $\delta$7.2 (S, 5H); 3.4 (d, 2H); 2.7 (S, 2H)

Anal calcd for C$_{19}$H$_{32}$N$_2$O$_2$: C, 71.21; H, 10.05; N, 8.74; Found: C, 71.62; H, 10.37; N, 8.27.

EXAMPLE 26

1-(Adamant-1'-ylmethyl)-2-(p-bromophenyl)hydrazine hydrochloride

The title compound was obtained in 75% yield by using p-bromophenylhydrazine instead of methylhydrazine as in Example 1.

mp 214°–215° (d), (isopropanol/methanol)

nmr (CDCl$_3$/TFA) $\delta$7.18 (q, 4H); 2.95 (s, 2H)

Anal calcd for C$_{17}$H$_{24}$N$_2$BrCl: C, 54.92; H, 6.44; N, 7.52; Cl, 9.50; Br, 21.51; Found: C, 54.53; H, 6.37; N, 7.31; Cl, 9.25; Br, 22.02.

EXAMPLE 27

1-(Adamant-1'-ylmethyl)-2-[4''-(7'''-chloroquinolinyl)]hydrazine hemi-hydrate The title compound was obtained in 17% yield by using 7-chloro-4-hydrazinoquinoline instead of methylhydrazine as in Example 1.

mp 308°–312° (d), (isopropanol)

nmr (CDCl$_3$) $\delta$8.6–8.9 (m, 1H), 7.9–8.2 (m, 2H), 7.0–7.4 (m, 2H), 2.7 (br.s., 2H)

Anal calcd for C$_{20}$H$_{26}$N$_3$Cl$_2$O$_{\frac{1}{4}}$: C,61.98; H,6.73; N,10.84; Found: C,61.52; H,6.17; N,10.39.

EXAMPLE 28

1-(Adamant-1'-ylmethylamino)-2-methylpyrrolidine hydrochloride

The title compound was obtained in 58% yield by using 1-amino-2-methylpyrrolidine instead of methylhydrazine as in Example 1.

mp 254°–256° (d), (isopropanol/ether)

nmr (CDCl$_3$/TFA) $\delta$ 3.2–4.0 (m, 3H); 2.6 (S, 2H); 1.4–2.5 (m, 22H)

mass spectrum (m/e) M+ =248 (64), 233 (78), 135 (65), 133 (100), 107 (38).

EXAMPLE 29

1-(Adamant-1'-ylmethylamino)homopiperidine hydrochloride quaterhydrate

The title compound was synthesized in 43% yield by using 1-amino-homopiperidine instead of methylhydrazine as in Example 1.

mp 265° (d), isopropanol)
nmr (CDCl$_3$) δ 2.75 (m, 4H), 2.5 (s, 2H)
Anal calcd for C$_{17}$H$_{31}$N$_2$Cl.¼H$_2$O: C,67.20; H,10.20; N,9.22; Found: C,67.24; H,10.19; N,9.07.

EXAMPLE 30

1-(Adamant-1'-ylmethylamino)heptamethyleneimine hydrochloride

The title compound was obtained in 16% yield using 1-aminoheptamethyleneimine instead of methylhydrazine as in Example 1, except that the resulting hydrazone was reduced with lithium aluminium hydride.

mp 285°-261° (d), (isopropanol/ethyl acetate)
nmr (CDCl$_3$) δ 3.0-3.6 (m, 4H), 2.7 (br.s. 2H)
Anal calcd for C$_{18}$H$_{33}$N$_2$Cl: N, 8.96; Found: N, 8.81.

EXAMPLE 31

1-(Adamant-2'-ylmethylamino)pyrrolidine hydrochloride

The title compound was obtained in 35% yield by using 2-adamantylaldehyde and 1-aminopyrrolidine instead of 1-adamantylaldehyde and methylhydrazine respectively as in Example 1 except that the resulting hydrazone was reduced with lithium aluminium hydride.

mp 235° (d), (ethylacetate)
nmr (CDCl$_3$) δ 2.8-4.0 (m, 6H)
Anal calcd for C$_{15}$H$_{27}$N$_2$Cl: C,66.54; H,9.98; N,10.35; Cl,13.12; Found: C,66.41; H,9.74; N,10.04; Cl,13.12.

EXAMPLE 32

1-(Adamant-2'-ylmethylamino)piperidine hydrochloride

The title compound was obtained in 20% yield using 2-adamantylaldehyde and 1-aminopiperidine instead of 1-adamantylaldehyde and methylhydrazine as in Example 1 except that the resulting hydrazone was reduced with lithium aluminium hydride.

mp 263°-264° (d), (isopropanol)
nmr (CDCl$_3$) δ 3.1-3.5 (m, 6H)
Anal calcd for C$_{16}$H$_{29}$N$_2$Cl: C,67.48; H,10.19; N,9.84; Cl,12.47; Found: C,67.31; H,10.35; N,9.78; Cl,12.91.

EXAMPLE 33

1-(Adamant-2'-ylmethyl)-2-(1''-adamantyl)hydrazine hydrochloride hemihydrate

The title compound was obtained in 5% yield using 2-adamantylaldehyde and 1-adamantylhydrazine instead of 1-adamantylaldehyde and methylhydrazine as in Example 1, except that the resulting hydrazone was reduced with lithium aluminum hydride.

mp 290°-292° (d), (methanol)
nmr (CDCl$_3$) δ 3.1 (d, 2H); 1.5-2.5 (m, 30H)
Anal calcd for C$_{21}$H$_{36}$N$_2$ClO$_{¼}$: C,70.09; H,10.01; N,7.78; Found: C,70.26; H,10.10; N,8.11

EXAMPLE 34

1-(Adamant-1'-ylmethylamino)thiomorpholine hydrochloride

The title compound was obtained in 38% yield using 1-aminothiomorpholine instead of methylhydrazine as in Example 1.

mp 269°-272° (d), (isopropanol/ethylacetate)
nmr (CDCl$_3$/TFA) δ 3.4-3.6 (m, 4H), 2.8—3.1 (m, 4H), 2.7 (br.s. 2H)
Anal calcd for C$_{15}$H$_{27}$N$_2$SCl: C,59.50; H,8.92; N,9.25; Cl,11.72; S,10.57; Found: C,59.23; H,8.73; N,8.91; Cl,12.00; S11.04

EXAMPLE 35

1-(Adamant-1'-ylmethylamino)hydantoin

The title compound was obtained in 10% yield using 1-aminohydantoin sulfate instead of methylhydrazine as in Example 1.

mp 193°-194° (d), (isopropanol)
nmr (CDCl$_3$/TFA) δ 4.5 (s, 2H); 3.2 (s, 2H).
Anal calcd for C$_{14}$H$_{22}$N$_3$O$_2$: C,63.59; H,8.40; N,15.89; Found: C,63.06; H,8.18; N,15.67.

EXAMPLE 36

1-(Adamant-1'-ylmethyl)-2-butylhydrazine hydrochloride hemi-demi-hydrate

The title compound was obtained in 39% yield using n-butylhydrazine hydrochloride (prepared in situ from the oxalate and conc. HCl) instead of methylhydrazine as in Example 1.

mp 236°-240° (d), (isopropanol)
nmr (CDCl$_3$/TFA) δ 3.2 (t, 2H); 2.7 (S, 2H)
Anal calcd for C$_{15}$H$_{29.5}$N$_2$ClO$_{¼}$: C,64.98; H,10.64; N,10.10; Found: C,64.71; H,10.38; N,10.04.

EXAMPLE 37

α-[2-(Adamant-1'-ylmethyl)hydrazino]butanoic acid hydrochloride

A methanolic solution of 1.64 g (10 mmol) of 1-adamantylaldehyde, 1.8 g (10 mmol) of ethyl hydrazinobutanoate hydrochloride and 5.6 g (10 mmol) of KOH was refluxed for 2½ hrs. The volatiles were removed in vacuo and the residue partitioned between methylene chloride and water. The organic layer was dried and concentrated to 3 g of hydrazone which was reduced with 750 mg of sodium cyanoborohydride. The resulting hydrazino ester was hydrolyzed by refluxing in 5 ml of conc. HCl for 30 min. Evaporation of the volatiles give the title compound in 75% yield.

mp 188°-190° (d), isopropanol/ethyl acetate)
nmr (CDCl$_3$/TFA) δ 4.0 (t, 1H); 2.9 (S, 2H); 1.0 (t, 3H).
Anal calcd for C$_{15}$H$_{27}$N$_2$O$_2$Cl: C,59.46; H,8.99; N,9.25; Cl,11.73; Found: C,59.52; H,8.81; N,9.20; Cl,12.85.

EXAMPLE 38

1-(Adamant-1'-ylmethyl)-1-isopropylhydrazine hydrochloride

A methanolic solution of 3 g (18 mmol) of adamant-1-ylmethylamine and 2 g (34 mmol) of acetone was refluxed for 2½ hours and the volatiles removed to give 3.6 g of imine, which was reduced with 550 mg of sodium borohydride in refluxing ethanol. After 1 hr. the volatiles were removed in vacuo and the residue partitioned between ether and water. The organic layer was dried and concentrated to 3.3 g of (adamant-1-ylmethyl)isopropylamine which was suspended in 30 ml of H$_2$O at 0° and 50% aq H$_2$SO$_4$ added until the suspension was acidic. At this time a solution of 1.5 g of sodium nitrite in 10 ml of H$_2$O was added forming a white precipitate. After 1 hr. at room temperature the mixture was extracted twice with methylene chloride and the organic layers dried and concentrated to 4.0 g of nitrosoamine which was subsequently reduced with 900 mg lithium aluminium hydride in refluxing tetrahydrofuran for 2 hrs. After cooling, sodium-sulfate decahydrate was added until bubbling ceased. Filtration and evaporation of the filtrate yielded 2.7 g of oil which was dissolved in ether and treated with HCl. The title compound was obtained in 58% yield by filtration.

mp 263°–264° (d), (isopropanol)

nmr (CDCl$_3$/TFA) δ 3.5 (m, 1H); 2.8 (S, 2H); 1.3 (d, 6H)

Anal calcd for C$_{14}$H$_{27}$N$_2$Cl: C,64.96; H,10.51; N,10.82; Cl,13.72; Found: C,64.70; H,10.64; N,10.71; Cl,13.50.

EXAMPLE 39

1-[(Adamant-1′-ylmethyl)methylamino]pyrrolidine hydrochloride

To a solution of 1.7 g (7.3 mmol) of 1-(adamant-1′-ylmethylamino)pyrrolidine in dry tetrahydrofuran under N$_2$ at 0° was added 6 ml (7.3 mmol) of 1.6 M butyllithium, followed in 5 min. by 0.8 ml (12.4 mmol) of methyliodide. After 15 min. at room temperature water was added and the mixture concentrated in vacuo and twice extracted with ether. The dried ether layers were combined treated with HCl to give the title compound which was obtained in 45% yield by filtration.

mp 227°–228° (d), (isopropanol/ethyl acetate)

nmr (CDCl$_3$) δ 3.4 (m, 4H); 2.8 (s, 3H); 2.5 (s, 2H)

Anal calcd for C$_{16}$H$_{29}$N$_2$Cl: C,67.44; H,10.26; N,9.83; Cl,12.47; Found: C,67.18; H,9.97; N,9.99; Cl,12.36.

EXAMPLE 40

1-(Adamant-1′-ylmethyl)-2-isopropylhydrazine hydrochloride

A methanolic solution of 1.4 g (6.5 mmol) of adamant-1-ylmethylhydrazine hydrochloride and 1 g (17 mmol) of acetone was refluxed for 4 hrs. The resulting hydrazone was reduced with sodium cyanoborohydride in ethanol. After 1 hr the reaction was basified with 10% NaOH, concentrated, and the residue partitioned between water and methylene chloride. The dried organic phase was concentrated dissolved in ether and treated with HCl. The title compound was obtained in 25% yield by filtration.

mp 237°–242° (ethylacetate/methanol).

nmr (CDCl$_3$/TFA) δ 3.5 (m, 1H); 2.6 (s, 2H); 1.4 (d, 6H)

Anal calcd for C$_{14}$H$_{27}$N$_2$Cl: C,64.99; H,10.44; N,10.83; Cl,13.75; Found: C,64.94; H,10.17; N,10.91; Cl,13.30.

EXAMPLE 41

1-(Adamant-1′-ylmethylamino)-3-methylpyrrolidine hydrochloride hemi-hydrate

A solution of 1.1 g (6.1 mmol) of adamant-1-ylmethylhydrazine and 700 mg (6.1 mmol) of methylsuccinic anhydride was refluxed in toluene with continuous removal of water via a Dean-Stark apparatus. After 2½ hrs the solution was diluted with ether, washed with saturated sodium carbonate, dried and concentrated to 1.1 g succinimide, which was reduced with 400 mg of lithium aluminium hydride in refluxing tetrahydrofuran for 3 hrs at which time the suspension was cooled and sodium sulfate decahydrate added until bubbling ceased. The mixture was then filtered and the filtrate concentrated and dissolved in ether and treated with HCl. The title compound was obtained in 22% yield by filtration.

mp 210°–215° (d), (ethylacetate)

nmr (CDCl$_3$) δ 8.2 (m, 3H, exch); 3.0–3.9 (m,4H); 2.9 (s, 2H); 1.2 (d, 3H)

Anal calcd for C$_{16}$H$_{30}$N$_2$ClO$_\frac{1}{2}$: C,65.37; H,10.28; N,9.53; Found: C,65.39; H,10.28; N,9.91.

In the following test results are given which demonstrate the antimicrobial, antiprotozoan, CNS, antifungal and antiviral activities of compounds according to the invention.

Antimicrobial activity was demonstrated on mycoplasma; antiprotozoan activity on Leishmania and Trypanosoma; CNS activity on albino rats and albino mice; antifungal activity on human fungi and yeast; and antiviral activity on HSV-1 (Herpes Simplex) and on influenza virus.

The following are the results:

ANTIMYCOPLASMA ACTIVITY

Some of the compounds were tested against 4 mycoplasma. The method used was as follows:

Microorganisms:
1. *M. gallisepticum*
2. *capricolum*
3. *M. hominis*
4. *A. laidlawii*

Assay:
50% inhibition of growth in liquid medium.

Results:
The tested compounds of Examples Nos. 3, 7, 8, 38, 25, were found to show a 50% inhibition in concentrations between 5–30 μg/ml, which are within the range of antibiotic activity.

ANTI LEISHMANIA AND ANTI TRYPANOSOMA TESTS

A. Scoring of drug activity:
  I. *L. tropica*
    a. amastigotes in peritoneal exudate cells in Mc Coy's medium in vitro at 37° C.
      +++ =clearance of all parasites in 24 hrs
      ++ =clearance of all parasites in 48 hrs
      + =clearance of all parasites in 72 hrs
      ± =partial clearance of parasites in 72 hours or more
      − =no activity against parasites.
    b. promastigotes in Mc Coy's medium in vitro at 27° C.
      +++ =no viable parasites after 24 hours
      ++ =no viable parasites after 48 hours
      + =no viable parasites after 72 hours
      ± =no viable parasites after 96 hours
      − =viable parasites after 120 hours.
  II. Trypanosoma in vitro
    Trypanosoma in RPMI medium in vitro at 37° C. Scoring as in b.

| ANTI LEISHMANIA AND ANTI TRYPANOSOMA TESTS | | | | | | |
|---|---|---|---|---|---|---|
| | Results: | | | | | |
| | Leishmania | | | | Trypanosoma | |
| Compound | Amastigote | | Promastigote | | in vitro | |
| of Ex. No. | 10 μg | 100 μg | 10 μg | 100 μg | 10 μg | 100 μg |
| 1 | ± | ± | — | +++* | ± | +++** |
| 14 | ± | ++ | | | +++ | +++* |
| 15 | | | — | +++ | | |
| Control Pentamidine | | +++ | +++ | +++ | — | ++ |

*An effect was observed with this drug after 1 h at this concentration. No effect was observed with Pentamidine at this time.
**Slight effect.

Summary:

The tested compounds of Examples Nos. 1, 14, 15 were found to be active against Leishmania.

The test compounds of Examples Nos. 1, 14 were found to be active against Trypanosoma.

ANTIPARKINSON ACTIVITY

Male Charles River albino rats, weighing 200–250 g, were used. Catalepsy was produced by haloperidol, 5 mg/kg i.p. The animals were placed with their front paws on a horizontal bar, about 10 cm above the ground, and animals were considered cataleptic if not changing posture for at least 30 sec. Cataleptic animals were injected l.p. with one of the drugs at a dose of 40–80 mg/kg. Catalepsy was estimated again at the intervals indicated.

| Drug: Control Symmetrel, Route, i.P., Dose: 80 mg/kg | | | | | |
|---|---|---|---|---|---|
| Time | Rat 1 | Rat 2 | Rat 3 | rat 4 | rat 5 |
| 0 | + | + | + | + | + |
| 45 | + | — | — | — | — |
| 90 | + | — | + | + | — |
| 110 | + | + | — | — | — |
| 180 | + | + | — | — | + |
| anticataleptic effect | 0/4 | 2/4 | ¾ | ¾ | ¾ |
| | | | Mean maximal effect | | 2.2/4 |

ANTI PARKINSON EVALUATION OF ANTICATALEPTIC EFFECT IN RATS

Male Charles River albino rats, wighing 200–250 g, were used. Catalepsy was produced by haloperidol, 5 mg/kg i.p. The animals were placed with their front paws on a horizontal bar, about 10 cm above the ground, and animals were considered cataleptic if not changing posture for at least 30 sec. Cataleptic animals were injected i.p. with one of the drugs at a dose of 40–80 mg/kg. catalepsy was estimated again at the intervals indicated.

| Drug: Compound of Example 7, Route: i.p., Dose: 80 mg/kg | | | | | |
|---|---|---|---|---|---|
| Time | rat 1 | rat 2 | rat 3 | rat 4 | rat 5 |
| 0 | + | + | + | + | + |
| 45 | — | + | + | + | + |
| 90 | + | + | + | + | — |
| 110 | + | + | + | + | — |
| 180 | + | + | + | + | — |
| Anticataleptic effect | ¼ | 0/4 | 0/4 | 0/4 | ¾ |
| | | | | mean maximal effect | 0.8/4 |

STEREOTYPED BEHAVIOUR IN MICE

Male ICR albino mice weighing 25–30 g were put in cages with a metal grid floor, 4 in each cage. Drugs were injected intraperitoneally and stereotyped behaviour (sniffing, biting, repetitive head movement) was evaluated every 30 min.

| Drug Control Symmetrel Route I.p. Dose 50 mg/kg | | | | |
|---|---|---|---|---|
| Time (min) | Mouse 1 | Mouse 2 | Mouse 3 | Mouse 4 |
| 0 | 0 | 0 | 0 | 0 |
| 30 | 1 | 1 | 1 | 1 |
| 45 | 1 | 1 | 1 | 1 |
| 60 | 2 | 2 | 1 | 1 |
| 90 | 1 | 1 | 2 | 1 |
| 120 | 2 | 2 | 2 | 2 |
| 135 | 2 | 2 | 2 | 2 |
| 150 | 2 | 2 | 2 | 2 |
| 180 | 2 | 2 | 2 | 2 |
| 210 | 2 | 2 | 2 | 1 |
| 240 | 2 | 2 | 2 | 0 |
| Total Score | 17 | 17 | 17 | 13 |
| | | | | Mean Score 16 |

| Drug Compound of Example 7 Route I.p. Dose 50 mg/kg | | | | |
|---|---|---|---|---|
| Time (min) | Mouse 1 | Mouse 2 | Mouse 3 | Mouse 4 |
| 0 | 0 | 0 | 0 | 0 |
| 30 | 2 | 0 | 0 | 0 |
| 45 | 2 | 0 | 1 | 0 |
| 60 | 2 | 0 | 0 | 0 |
| 90 | 2 | 2 | 0 | 0 |
| 120 | 2 | 2 | 0 | 0 |
| 135 | 2 | 2 | 0 | 0 |
| 150 | 2 | 2 | 1 | 0 |
| 180 | 1 | 1 | 1 | 0 |
| 210 | 1 | 1 | 2 | 2 |
| 240 | 1 | 1 | 1 | 1 |
| Total Score | 17 | 11 | 6 | 3 |
| | | | | Mean Score 9.25 |

Summary:

The tested compound of Example 7 was found to be active.

ANTIMYCOTIC ACTIVITY (Human)

The method for the evaluation was as follows:

Microorganisms:
1. Candida albicans
2. Trichophyton rubrum
3. Trichophyton mentagrophytes.

Assay:

Concentrations of 10 μg/ml, 50 μg/ml, 100 μg/ml, of each of the tested compounds were mixed in a Sabouraud dextrose agar, on which the test organisms were inoculated.

Evaluation:

Control (full growth): ++++

No growth:

The results are summarized in the following table:

| ANTI HUMAN FUNGI AND YEAST | | | | |
|---|---|---|---|---|
| Compound of Example No. | Concent. μg/ml | C. albicans | T. rubrum | T. mentagrophytes |
| Control | 10 | ++++ | ++++ | ++++ |

|  | -continued | | | |
|---|---|---|---|---|
| ANTI HUMAN FUNGI AND YEAST | | | | |
| Compound of Example No. | Concent. µg/ml | C. albicans | T. rubrum | T. menta grophytes |
|  | 50 | ++++ | ++++ | ++++ |
|  | 100 | ++++ | ++++ | ++++ |
| 1. 3 | 10 | ++++ | +++ | +++ |
|  | 50 | ++++ | ++ | ++ |
|  | 100 | ++++ | + | ++ |
| 2. 8 | 10 | ++++ | ++++ | ++++ |
|  | 50 | ++++ | ++ | ++ |
|  | 100 | ++++ | ± | ± |
| 3. 16 | 10 | ++++ | ++ | +++ |
|  | 50 | ++++ | + | + |
|  | 100 | +++ | + | ± |
| 4. 38 | 10 | ++++ | ++++ | ++++ |
|  | 50 | ++++ | ++ | ± |
|  | 100 | ++++ | ++ | ± |

Results:

The results indicate that the tested compounds of Examples 3, 8, 16, 38 demonstrate an activity in the range of 50–100 µg/ml.

| INHIBITION TEST ON HSV REPLICATION | |
|---|---|
| Cells | - BSC-1 (Green monkey Kidney) |
| Virus | - HSV-1 (Herpes Simplex) |
| Inoculum | - 10 PFU/cell |
| Medium | - DMEM + 10% C.S. |
|  | Herpes |
|  | J. Levitt & Y. Becker |
|  | Virology 31, 129–134 (1967) |

| Compound of Example No. | Concent µg/ml | T.L. µg/ml* Toxic Limit | % Inhibition** |
|---|---|---|---|
| Ex. 7 | 100 | 50 | 99.9 |
|  | 75 |  | 98 |
|  | 50 |  | 92 |
|  | 25 |  | 72.5 |
| Ex. 31 | 100 |  | 97 |
|  | 50 |  | 91 |
|  | 25 |  | 51 |

*T.L. The highest concentration of compound which is completely not toxic.
**% Inhibition of control infected for some time with same virus PFV with no inhibition.

Results

The tested compounds of Examples 7, 31 were found to inhibit HSV by 96–99% at a concentration of 50–200 µg/ml.

Anti-influenza virus effects (preliminary results)

Method:
G. Appleyard and Maber J. of Gen. Virol. 25, 351–357 (1974).

The tested compounds of Examples 7, 31, 23, 29, 38, 41, 8 were found effective against influenza A virus at a concentration of 10–50 µg/ml.

We claim:

1. A 1- or 2-Adamantylmethyl hydrazine of the general formula A

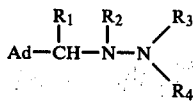

wherein Ad is 1- or 2-adamantyl, $R_1$ and $R_2$ are the same or different and are each hydrogen or a lower unsubstituted or substituted alkyl group of 1–4 carbon atoms; $R_3$ and $R_4$ are the same or different and are each hydrogen, an unsubstituted or substituted radical being a lower alkyl of 1–4 carbon atoms, a lower alkanoic acid radical or 2–4 carbon atoms or a lower alkyl ester thereof, adamantyl, phenyl, phenethyl, benzyl or an unsubstituted or substituted pyridyl or quilonilyl; or $R_3$ and $R_4$ together with the nitrogen atom to which they are attached form a cyclic radical; or a pharmaceutically acceptable acid addition salt thereof.

2. A compound in accordance with claim 1 wherein $R_3$ or $R_4$ is a substituted radical wherein the substituent is selected from the group consisting of trifluoromethyl, carboxy, methyl, hydroxy, bromo and chloro.

3. A compound in accordance with claim 1 wherein the cyclic radical formed by $R_3$ and $R_4$ together with the nitrogen atom, is selected from the group consisting of piperidino, homopiperidino, pyrrolidino, morpholino, thiomorpholino, hydantiono, piperazino and heptamethyleneimino.

4. 1-(Adamant-1'-ylmethyl)-2-methylhydrazine or a pharmaceutically acceptable acid addition salt thereof, in accordance with claim 1.

5. 1-(Adamant-1'-ylmethyl)-2,2-dimethylhydrazine or a pharmaceutically acceptable acid addition salt thereof, in accordance with claim 1.

6. 1-(Adamant-1'-ylmethyl)-2-benzylhydrazine or a pharmaceutically acceptable acid addition salt thereof, in accordance with claim 1.

7. 1-(Adamant-1'-ylmethyl)-2,2-diphenylhydrazine or a pharmaceutically acceptable addition salt thereof, in accordance with claim 1.

8. 1-(Adamant-1'-ylmethyl)-2-(m-trifluoromethylphenyl)hydrazine or a pharmaceutically acceptable acid addition salt thereof, in accordance with claim 1.

9. 1-(Adamant-1'-ylmethyl)-2-(o-carboxyphenyl)hydrazine or a pharmaceutically acceptable acid addition salt thereof, in accordance with claim 1.

10. 1-(Adamant-1'-ylmethylamino)pyrrolidine or a pharmaceutically acceptable acid addition salt thereof, in accordance with claim 1.

11. 1-(Adamant-1'-ylmethylamino)piperidine or a pharmaceutically acceptable acid addition salt thereof, in accordance with claim 1.

12. 4-(Adamant-1'-ylmethylamino)morpholine or a pharmaceutically acceptable acid addition salt thereof, in accordance with claim 1.

13. 1-(Adamant-1'-ylmethylamino)-4-methylpiperazine or a pharmaceutically acceptable acid addition salt thereof, in accordance with claim 1.

14. 1-(Adamant-1'-ylmethylamino)-4-(m-trifluoromethyl)piperazine or a pharmaceutically acceptable acid addition salt thereof, in accordance with claim 1.

15. 1-(Adamant-2'-ylmethyl)-2,2-dimethylhydrazine or a pharmaceutically acceptable acid addition salt thereof, in accordance with claim 1.

16. 1-(Adamant-2'-ylmethyl)-2-(pyrid-2'''-yl)hydrazine or a pharmaceutically acceptable acid addition salt thereof, in accordance with claim 1.

17. (Adamant-1'-ylmethyl)hydrazine or a pharmaceutically acceptable acid addition salt thereof, in accordance with claim 1.

18. 1-(Adamant-1'-ylmethyl)-1-methylhydrazine or a pharmaceutically acceptable addition salt thereof, in accordance with claim 1.

19. 1-(Adamant-2'-ylmethyl)-1-methylhydrazine or a pharmaceutically acceptable acid addition salt thereof, in accordance with claim 1.

20. Ethyl [2-(adamant-1'-ylmethyl)hydrazino]acetate or a pharmaceutically acceptable acid addition salt thereof, in accordance with claim 1.

21. [2-(Adamant-1'-ylmethyl)hydrazino]acetic acid or a pharmaceutically acceptable acid addition salt thereof, in accordance with claim 1.

22. 1,1-Dimethyl-2-(adamant-2'-ylmethyl)hydrazine or a pharmaceutically acceptable acid addition salt thereof, in accordance with claim 1.

23. [1-(Adamant-1'-yl)ethyl]hydrazine or a pharmaceutically acceptable acid addition salt thereof, in accordance with claim 1.

24. 1-[1'-(Adamant-1''-yl)ethyl]-2-methylhydrazine or a pharmaceutically acceptable acid addition salt thereof, in accordance with claim 1.

25. 1-[1'-(Adamant-1''-yl)ethyl]-2-(m-trifluoromethylphenyl)hydrazine or a pharmaceutically acceptable acid addition salt thereof, in accordance with claim 1.

26. 1-(Adamant-1'-ylmethyl)-2-[1''-(2'''-hydroxyethyl)]hydrazine or a pharmaceutically acceptable acid addition salt thereof, in accordance with claim 1.

27. 1-(Adamant-1'-ylmethyl)-2-phenethylhydrazine or a pharmaceutically acceptable acid addition salt thereof, in accordance with claim 1.

28. 1-(Adamant-1'-ylmethyl)-2-(p-bromophenyl)hydrazine or a pharmaceutically acceptable acid addition salt thereof, in accordance with claim 1.

29. 1-(Adamant-1'-ylmethyl)-2-[4''-(7''-chloroquinolinyl)]hydrazine or a pharmaceutically acceptable acid addition salt thereof, in accordance with claim 1.

30. 1-(Adamant-1'-ylmethylamino)-2-methylpyrrolidine or a pharmaceutically acceptable acid addition salt thereof, in accordance with claim 1.

31. 1-(Adamant-1'-ylmethylamino)homopiperidine or a pharmaceutically acceptable acid addition salt thereof, in accordance with claim 1.

32. 1-(Adamant-1'-ylmethylamino)heptamethyleneimine or a pharmaceutically acceptable acid addition salt thereof, in accordance with claim 1.

33. 1-(Adamant-2'-ylmethylamino)pyrrolidine or a pharmaceutically acceptable acid addition salt thereof, in accordance with claim 1.

34. 1-(Adamant-2'-ylmethylamino)piperidine or a pharmaceutically acceptable acid addition salt thereof, in accordance with claim 1.

35. 1-(Adamant-2'-ylmethyl)-2-(1'''-adamantyl)hydrazine or a pharmaceutically acceptable acid addition salt thereof, in accordance with claim 1.

36. 1-(Adamant-1'-ylmethylamino)thiomorpholine or a pharmaceutically acceptable acid addition salt thereof, in accordance with claim 1.

37. 1-(Adamant-1'-ylmethylamino)hydantoin or a pharmaceutically acceptable acid addition salt thereof, in accordance with claim 1.

38. 1-(Adamant-1'-ylmethyl)-2-butylhydrazine or a pharmaceutically acceptable acid addition salt thereof, in accordance with claim 1.

39. α-[2-(Adamant-1'-ylmethyl)hydrazino]butanoic acid or a pharmaceutically acceptable acid addition salt thereof, in accordance with claim 1.

40. 1-(Adamant-1'-ylmethyl)-1-isopropylhydrazine or a pharmaceutically acceptable salt addition salt thereof, in accordance with claim 1.

41. 1-[(Adamant-1'-ylmethyl)methylamino]pyrrolidine or a pharmaceutically acceptable acid addition salt thereof, in accordance with claim 1.

42. 1-(Adamant-1'-ylmethyl)-2-isopropylhydrazine or a pharmaceutically acceptable acid addition salt thereof, in accordance with claim 1.

43. 1-(Adamant-1'-ylmethylamino)-3-methylpyrrolidine or a pharmaceutically acceptable acid addition salt thereof, in accordance with claim 1.

44. A biocidal composition containing as active ingredient a biocidally effective amount of a compound according to claim 1 and a pharmaceutical carrier therefor.

* * * * *